(12) United States Patent
Lewis et al.

(10) Patent No.: US 11,154,225 B2
(45) Date of Patent: Oct. 26, 2021

(54) TRANSDERMAL BIOSENSOR

(71) Applicant: The Regents of the University of Colorado, Denver, CO (US)

(72) Inventors: Stephen Michael Lewis, Denver, CO (US); Andrew John Henderson, Denver, CO (US); Jenny B. Filipetti, Denver, CO (US)

(73) Assignee: The Regents of the University of Colorado, Denver, CO (US)

( * ) Notice: Subject to any disclaimer, the term of this patent is extended or adjusted under 35 U.S.C. 154(b) by 326 days.

(21) Appl. No.: 16/449,140

(22) Filed: Jun. 21, 2019

(65) Prior Publication Data

US 2019/0388016 A1    Dec. 26, 2019

Related U.S. Application Data

(60) Provisional application No. 62/688,414, filed on Jun. 22, 2018.

(51) Int. Cl.
| | |
|---|---|
| *A61B 5/145* | (2006.01) |
| *A61B 5/00* | (2006.01) |
| *G01N 33/66* | (2006.01) |
| *G01N 21/77* | (2006.01) |
| *G01N 21/78* | (2006.01) |
| *G01N 33/58* | (2006.01) |

(52) U.S. Cl.
CPC .......... *A61B 5/14546* (2013.01); *A61B 5/441* (2013.01); *A61B 5/4845* (2013.01); *A61B 5/6831* (2013.01); *A61B 5/681* (2013.01); *G01N 21/78* (2013.01); *G01N 33/582* (2013.01); *G01N 33/66* (2013.01); *G01N 2021/7756* (2013.01); *G01N 2021/7796* (2013.01)

(58) Field of Classification Search
CPC ......... A61B 5/145; A61B 5/00; A61B 5/6831; A61B 5/14546; A61B 5/441; A61B 5/14532; A61B 5/4845; A61B 5/681; G01N 33/98; G01N 21/76; G01N 2021/7756; G01N 33/66; G01N 2021/7796; G01N 33/582; G01N 21/78; C12Q 1/26
See application file for complete search history.

(56) References Cited

U.S. PATENT DOCUMENTS

| | | | |
|---|---|---|---|
| 5,944,661 A | 8/1999 | Swette et al. | |
| 6,750,311 B1 * | 6/2004 | Van Antwerp | G01N 33/66 427/2.12 |
| 6,999,810 B2 | 2/2006 | Berner et al. | |
| 7,873,399 B2 | 1/2011 | Berner et al. | |
| (Continued) | | | |

FOREIGN PATENT DOCUMENTS

EP    1102561 B1    11/2003

*Primary Examiner* — Eric J Messersmith
(74) *Attorney, Agent, or Firm* — Holland & Hart LLP

(57) ABSTRACT

The disclosed technology includes device, systems, and methods for detecting an analyte using a biosensor. In some implementations, the biosensor may be a transdermal biosensor including a housing material, a nanocellulose material disposed within the housing material, an enzyme entrapped within the nanocellulose material that produces a chemical or biological product when exposed to a vapor or liquid, and a luminescent material within the nanocellulose material that emits visible light upon a chemical or biological reaction with the chemical or biological product.

20 Claims, 5 Drawing Sheets

(56) References Cited

U.S. PATENT DOCUMENTS

| | | | | |
|---|---|---|---|---|
| 10,098,574 | B1* | 10/2018 | Kam | A61B 5/1455 |
| 2015/0087935 | A1* | 3/2015 | Davis | A61B 5/445 |
| | | | | 600/309 |
| 2016/0287152 | A1* | 10/2016 | Schwartz | A61B 5/14546 |
| 2016/0313358 | A1* | 10/2016 | Titmus | G01N 33/98 |
| 2017/0248524 | A1 | 8/2017 | Le | |

* cited by examiner

TRANSDERMAL BIOSENSOR

CROSS-REFERENCE TO RELATED APPLICATION

This application claims the benefit of U.S. Provisional Patent Application No. 62/688,414 entitled "A modular biological, chemical, and/or electronic sensor platform, and corresponding method and process for fabrication, testing, validation, and manufacturing," filed on Jun. 22, 2018 and is specifically incorporated by reference for all it discloses and teaches.

TECHNICAL FIELD

This relates to a sensing device that can be used with chemical or biological compounds to detect a reactant. In particular, it relates to a transdermal biosensor.

BACKGROUND

Diagnostic tests may be routinely performed on individuals to evaluate the amount of substances present in blood or other body fluids. The diagnostic tests may rely on physiological fluid samples removed from the subject (e.g., via a syringe or by pricking the skin). In some examples, alcohol consumption may be monitored in individuals by direct measurement of urine, blood, saliva, or sweat alcohol levels.

Methods are needed to effectively and accurately monitor alcohol consumption (e.g., blood alcohol concentration (BAC)) in individuals. Traditionally, individuals may utilize electronic-based alcohol sensing devices. However, electronic-based alcohol sensing devices may be prone to errors and expensive to produce. In some cases, the manufacturing process for electronic-based alcohol sensing devices may negatively impact the environment. Therefore, a cost effective and environment friendly alcohol sensing device could serve as an attractive alternative to monitor BAC in individuals, potentially leading to preventative measures for drunk driving, encouraging responsible drinking in individuals, and social accountability.

SUMMARY

The disclosed technology is directed to a biosensor. In some implementations, the biosensor may include a housing material, a nanocellulose material disposed within the housing material, an enzyme entrapped within the nanocellulose material that produces a chemical or biological product when exposed to a vapor or liquid, and a luminescent material within the nanocellulose material that emits visible light upon a chemical or biological reaction with the chemical or biological product. In some implementations, the vapor or liquid comprises ethanol. In some implementations, the enzyme comprises alcohol oxidase. In some implementations, the nanocellulose material comprises bacterial nanocellulose. In some implementations, the bacterial nanocellulose immobilizes the enzyme within the bacterial nanocellulose. In some implementations, the chemical or biological product of the reaction with the enzyme comprises hydrogen peroxide. In some implementations, the luminescent material comprises an oxalate and a fluorophore, wherein the resulting luminescent material is a chemiluminescent or bioluminescent material.

In some implementations, the biosensor further comprises one or more solvents that facilitate the chemical or biological reaction of the luminescent material and the chemical or biological product. In some implementations, the housing material comprises a polymer. In some implementations, the housing material forms a wristband. In some implementations, the biosensor further comprises a recessed portion disposed on a side of the wristband that is adjacent to a skin surface of a wearer, wherein the recessed portion is configured to capture the vapor or liquid evaporating from the skin surface of the wearer. In some implementations, the biosensor is biodegradable. In some implementations, the biosensor is a transdermal biosensor.

In some implementations, a method of fabricating a biosensor may include growing a portion of nanocellulose, exchanging water within the portion of nanocellulose with one or more solvents, doping the portion of nanocellulose with an enzyme that is nonreactive with the one or more solvents, doping the portion of nanocellulose with a luminescent material, and compressing the portion of nanocellulose. In some implementations, the method may include stamping a shape from the compressed portion of nanocellulose or patterning a shape onto the compressed portion of nanocellulose. In some implementations, the one or more solvents comprise a phthalate or ethyl acetate. In some implementations, the luminescent material comprises an oxalate and a fluorophore.

In some implementations, a method of fabricating a biosensor may include growing a portion of nanocellulose, exchanging water within the portion of nanocellulose with one or more solvents, doping the portion of nanocellulose with a luminescent material, compressing and stamping the portion of nanocellulose, and then doping a portion of the stamped, doped nanocellulose with an enzyme that is nonreactive with the one or more solvents. In some implementations, the method may include adding dispersed and solvent exchanged nanocellulose onto the enzyme and biosensor. In some implementations, the one or more solvents comprise a phthalate or ethyl acetate.

In some implementations, a modular biosensor system may include a housing material comprising one or more module inserts and one or more biosensor modules removably coupled with the one or more module inserts, wherein the one or more biosensor modules each comprise a matrix material, an enzyme within the matrix material that produces a chemical or biological product when exposed to a detectable reactant, and an indicator material that indicates a change upon a reaction with the chemical or biological product. In some implementations, the matrix material immobilizes the enzyme within the matrix material. In some implementations, the detectable reactant comprises ethanol, glucose, dermal microbiota, toxins, a chemical or biological compound associated with a medical condition, nutrients, metabolic by-products, hormones, environmental ligands, or a combination thereof. In some implementations, the indicator material that indicates the change comprises luminescence, a color change, an electrical change, a chemical change, or a combination thereof. In some implementations, the matrix material comprises bacterial cellulose, chitosan, glutaraldehyde, agarose, alginate, kombucha pellicle, or a combination thereof.

These and various other features and advantages will be apparent from a reading of the following detailed description.

DRAWINGS

Implementations are disclosed in association with the accompanying drawings in which.

DETAILED DESCRIPTION

Definitions

Figure 1:
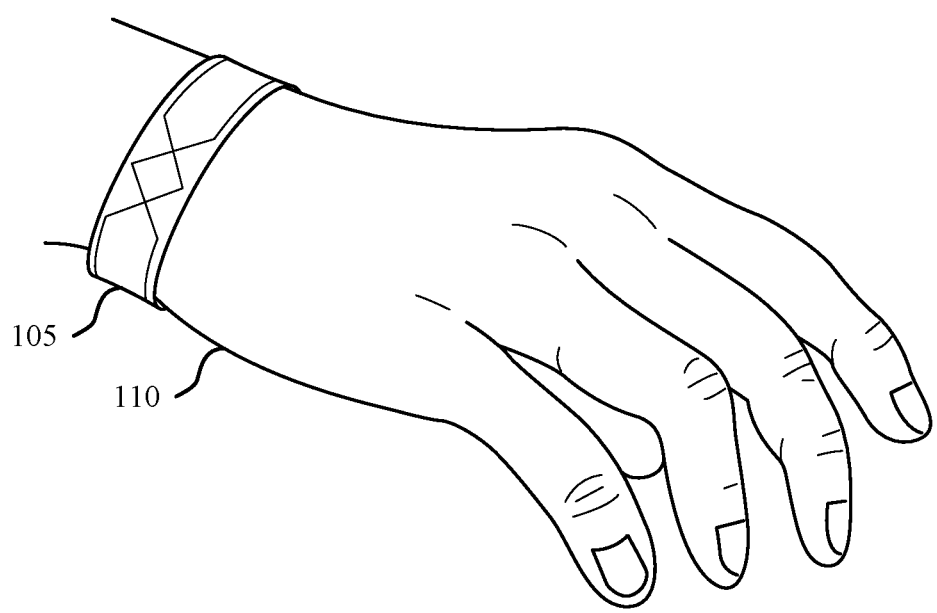
FIG. 1 illustrates a system including a biosensor in accordance with aspects in the present disclosure.
Figure 1:

The term "biosensor" or "biosensor module" refers to any device which utilizes a biologically derived component for obtaining a sample from a system for the purpose of determining the concentration of a detectable reactant of interest (e.g. any ligand). The biosensor may refer to a system useful for continually or continuously measuring a physiological detectable reactant present in the system.

The term "transdermal" refers to both transdermal and transmucosal techniques such as extraction of a target detectable reactant across skin or mucosal tissue.

The term "detectable reactant" or "analyte" refers to any physiological ligand of interest that is a specific substance or component that is being detected and/or measured in a biological, chemical, physical, enzymatic, or optical analysis. A detectable signal (e.g., a biological signal, chemical signal, or electrochemical signal) can be obtained, either directly or indirectly, from such analyte or derivative.

The terms "reactant" or "substrate" refer to a substance that takes part and undergoes change during a chemical or biological reaction. The molecules upon which enzymes may act on are called substrates or reactants. Reactants may transform into products after passing through a high energy transition state.

The term "product" refers to a substance that is formed as the result of a chemical or biological reaction. The enzyme converts substrates into different molecules known as products.

The term "housing" refers to a material or casing that encloses and protects the components of the biosensor. The housing may also display the visible change due to the reaction between chemical compounds and the enzymes.

The terms "entrapment", "immobilized", and "immobilization" refer to physically trapping relatively small chemical or biological compounds (e.g., enzymes) within a web of the matrix material. An immobilized enzyme is an enzyme held in place within an inert, insoluble material that allows the enzyme to be held in place throughout the entire reaction.

The term "cellulose" refers to an insoluble substance which is the main constituent of plant cell walls and of vegetable fibers. Cellulose is an organic compound polysaccharide that consists of a linear chain of several hundred to several thousand of beta linked D-glucose units.

The term "nanocellulose" refers to a light solid substance obtained from plant matter which includes nanosized cellulose fibrils. Bacterial nanocellulose is a type of nanostructured cellulose produced by bacteria.

The terms "enzyme" and "catalyst" refer to a substance produced by a living organism which acts to bring about a specific biochemical reaction. Enzymes accelerate reactions without undergoing any permanent structural change. Enzymes and catalysts lower the energy level to transform reactants into products.

The term "oxidase" refers to an enzyme that catalyzes a chemical reaction. An oxidase is an enzyme that promotes the transfer of a hydrogen atom from the substrate to an oxygen atom.

The term "solvent" refers to a substance that dissolves a solute (e.g., chemically distinct liquid, solid, or gas) to form a solution. A solvent can be liquid, solid, or gas.

The term "solvent exchange" refers to a method to systematically replace the liquid phase of a gel with another liquid with minimal perturbations to the solid polymer component of the gel.

The term "luminescence" refers to the emission of light as a result of a reaction. The visible light is visible to the naked eye. During the reaction, an excited molecule may return to ground state by energy as light. Bioluminescence and chemiluminescence may be examples of luminescence.

The term "luminescent material" refers to a mixture or solution of compounds capable of producing light or luminescence under the proper conditions. Bioluminescent and chemiluminescent materials may be examples of luminescent materials.

The term "chromogenic" refers to a colorless chemical that enzymes may convert to a colored chemical. Chromogenic may involve the production of color or pigments.

The term "doping" refers to the process of adding impurities to a substance to alter the properties of the compound.

The terms "individual", "subject", "wearer", and "user" are used interchangeably herein and refer to any mammalian subject for whom use of the biosensor is desired, particularly humans. The terms may refer to non-mammalian organisms or environmental applications.

The terms "a", "an", and "the" refer to embodiments having plural referents, unless the content clearly dictates otherwise. As used in this specification and the appended claims, the term "or" is generally employed in its sense including "and/or" unless the content clearly dictates otherwise.

The term "approximately" refers to a particular measurement, time, or number that is close to the recited measurement but is not exact.

The following description provides specific embodiments. It is to be understood that other embodiments are contemplated and may be made without departing from the scope or spirit of the present invention. The following detailed description, therefore, is not to be taken in a limiting sense. While the present invention is not so limited, an appreciation of various aspects of the invention will be gained through a discussion of the examples provided below.

Conventional biosensors may include electronic circuitry that can only track a small range or type of data. Furthermore, typical electronic based biosensors may suffer from false positives and other sensing errors (e.g., sodium ions emitted from sweat may produce a false positive due to ion changes in the skin surface). In some cases, quantifying the information tracked by typical biosensors containing electronic circuitry may raise concerns about privacy of personal data because the information may be stored locally (e.g., in the device memory) or remotely (e.g., to a server). Electronic-based sensors may also contribute to the pollution from manufacturing, material waste associated with the manufacturing process, and the leaching of toxic materials after disposal.

In accordance with aspects of the present disclosure, to address some or all of these shortcomings, a biosensor is described that may effectively and accurately monitor physiological conditions of an individuals as well as environmental conditions. For example, the biosensor may be worn by an individual, or the biosensor may be placed within an environment to monitor the surrounding conditions (e.g., an industrial monitoring context). The biosensor may be biodegradable such that the biosensor is made of biological enzymes and chemical or biological compounds. In such cases, the biosensor may decrease the pollution from manufacturing, decrease material waste associated with the manufacturing process, and decrease the leaching of toxic materials after disposal. Additionally, the biosensor may not contain electronic circuitry, thereby decreasing the cost, decreasing the weight, and requiring less user decisions and action than if the biosensor included electronic circuitry.

The biosensor may comprise a polymeric housing material, a nanocellulose material, an enzyme, and a luminescent material. The nanocellulose material may be disposed within the housing material, and the enzyme may be entrapped within a matrix of the nanocellulose material. The biosensor may be tunable depending on the physical, biological, or chemical properties of the nanocellulose material, the enzyme, and the luminescent material to detect a variety of medical conditions. For example, the material of each component may be selected based on the needs of the individual.

In some cases, the physiological condition of the individual may be monitored or detected by capturing a vapor or liquid excreted through the skin surface of the individual. The vapor or liquid may be captured within the biosensor. For example, the nanocellulose material within the housing material may capture the vapor or liquid evaporated from the skin surface. For example, the nanocellulose material may capture ethanol vapor or liquid.

The enzyme may react with the vapor or liquid to produce a chemical or biological product. In some examples, the enzyme may be alcohol oxidase, and the chemical or biological product may be hydrogen peroxide. The nanocellulose material may also house the reactants that produce luminescent material. The chemical or biological product may react with the luminescent material where the luminescent material may be an oxalate (e.g., bis-[2,4,5-trichloro-6-(pentyloxycarbonyl)phenyl]oxalate (CPPO)) and a fluorophore. The product of the reaction between the chemical or biological product and the luminescent material may emit a visible light (e.g., glow). The visible light may be seen by the naked eye. For example, the visible light may not require a sensor or electronic circuitry to observe the visible light.

In some cases, the biosensor may be a wristband wearable by a user. For example, the user may wear the biosensor around the wrist at social functions, concerts, or bars to detect the blood alcohol concentration (BAC) of the user. When the biosensor begins to glow (e.g., indicating a chemical or biological reaction between the ethanol and the enzyme), the user may have a BAC level that may impair the user's decision making ability. In such cases, the biosensor may prevent drunk driving, encourage responsible drinking, and encourage personal and social accountability. Additionally, the results of the biosensor may be displayed in the biosensor itself, thereby localizing the results to be discreet and personal to the wearer.

FIG. 1 illustrates a system 100 including a biosensor 105 in accordance with aspects in the present disclosure. The system 100 may include the biosensor 105 and the wearer 110. The system 100 may be configured to detect a reactant, via the biosensor 105, from a skin surface of the wearer 110 of the biosensor 105. In some cases, the biosensor 105 may be a transdermal biosensor.

The biosensor 105 may be an example of a wristband that is positioned around the wrist of the wearer 110. In such cases, the biosensor 105 may be a wearable biosensor. The biosensor 105 may also be positioned around the ankle of the wearer 110, the neck of the wearer 110, or a different part of the body of the wearer 110 where the reactant may be detected. In some cases, the biosensor 105 is adjacent to the skin surface of the wearer 110. In other examples, the biosensor 105 may be directly applied to the skin surface of the wearer 110 in the form of a tattoo or ink applied to the skin surface. In such cases, the biosensor 105 may not be required to be worn around a part of the body of the wearer 110.

The biosensor 105 may be biodegradable. For example, the biosensor 105 may be made of biodegradable materials that are grown from biological processes. For example, the biosensor 105 may be made of naturally grown materials, biological enzymes, and other biodegradable components. Because the biosensor 105 is biodegradable, the biosensor 105 may decrease the pollution from manufacturing, decrease material waste associated with the manufacturing process, and decrease the leaching of toxic materials after disposal. The biosensor 105 may include chemical compounds that react with detectable reactants to produce a chemical change, a color change, an electrical change, luminescence, or a combination thereof that is visibly noticeable in the wristband. Chemical compounds may be an example of biological compounds.

In some cases, the biosensor 105 may be used to detect a blood alcohol concentration (BAC) level of the wearer 110. The biosensor 105 may be an example of an alcohol-sensing wristband. The wearer 110 may wear the biosensor 105 around the wrist at social gatherings, restaurants, parties, concerts, or bars. When the biosensor 105 begins to glow, the wearer 110 may have a BAC level that may impair the wearer's 110 decision making and/or driving ability. In such cases, the biosensor 105 may prevent drunk driving, encourage responsible drinking, and encourage personal and social accountability.

In other examples, the biosensor 105 may be used to detect glucose, microbiota, drug levels, disease, other medical conditions associated with the wearer 110, or a combination thereof. In such cases, the biosensor 105 may be tunable to address the conditions and needs of the wearer 110. For example, the wearer 110 may choose a chemical or biological compound (e.g., matrix material, enzyme, luminescent material) to be placed within the biosensor 105 that reacts with detectable reactants (e.g., glucose, dermal microbiota, toxins, a chemical or biological compound associated with a medical condition) emitted from the skin surface of the wearer 110. Depending on the reaction of the selected chemical or biological compound and the detectable reactant, the visible change in the biosensor may be a chemical change, color change, or an electrical change.

The biosensor 105 may not contain electronic circuitry, thereby decreasing the cost, decreasing the weight, and requiring less user decisions and action than if the biosensor 105 included electronic circuitry. Conventional methods that include electronic circuitry may be limited to tracking a small range of data that can be measured electronically. Thus, electronic-based consumer sensors may be limited to the kind of stimuli the sensors measure and transduce. In such cases, wearers 110 interested in quantifying their health and habits may be confined to commercial applications, which may raise concerns about privacy of personal data. Instead, the results of the biosensor 105 may be displayed in the biosensor 105 itself, thereby localizing the results to be discreet and personal to the wearer 110 without requiring that the personal data be transmitted or stored either locally (e.g., in device memory) or remotely (e.g., to a server).

Figure 2:
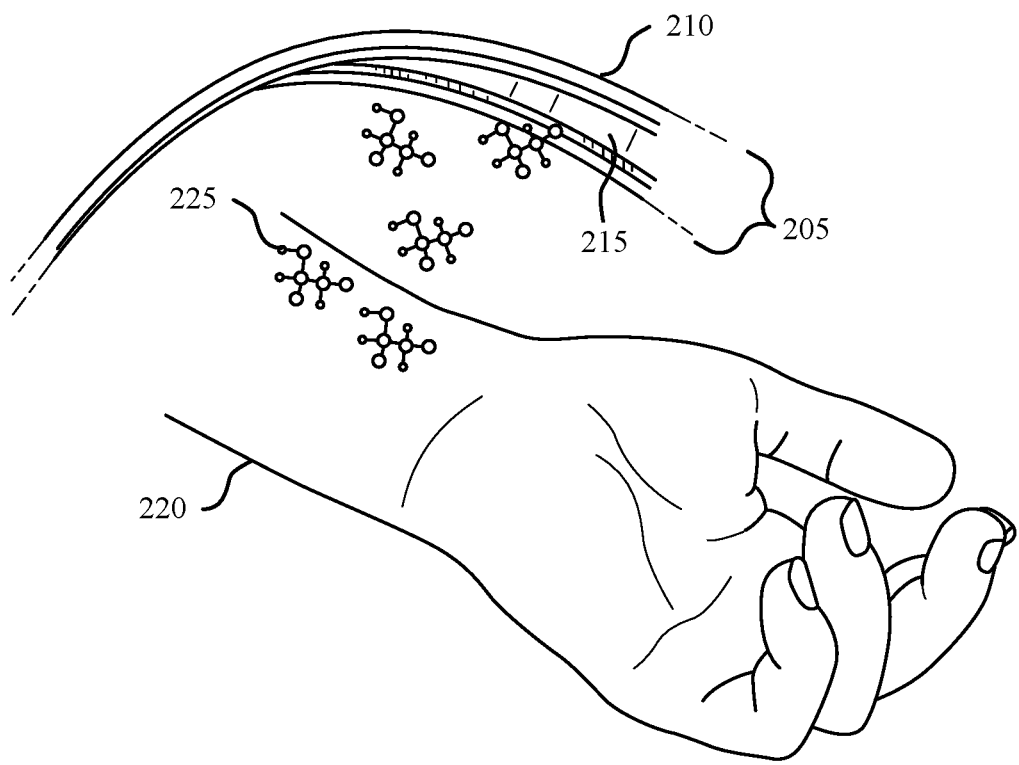
FIG. 2 illustrates a system for detecting a reactant in accordance with aspects in the present disclosure.

FIG. 2 illustrates a system 200 for detecting a reactant in accordance with aspects in the present disclosure. The system 200 includes a biosensor 205 where the biosensor 205 may be an example of the biosensor 105 described with reference to FIG. 1. The biosensor 205 may include a housing material 210 and a recessed portion 215. The system 200 may also include a skin surface 220 and vapor 225. In accordance with various examples, system 200 may be used to detect transdermal reactants.

The biosensor 205 may include the housing material 210. The housing material 210 may from a wristband made of a flexible, polymer material. For example, the housing material 210 may be made of silicone, acrylate, cellulose, cellulose acetate, nafion, vinyl, elastane, urethane, metal, thermoplastics (e.g., polylactic acid, thermoplastic polyurethane, nylon, acrylonitrile butadiene styrene), or a combination thereof. In such cases, the housing material 210 may be multi-material to allow for a tunable rigidity and porosity. In some cases, the housing material 210 may include chemical compounds, biological enzymes, and other biological components that may detect transdermal reactants and produce a visible change in the biosensor 205. Chemical compounds may be an example of biological compounds.

The biosensor 205 may include a recessed portion 215. The recessed portion 215 may be located on a side of the wristband (e.g., biosensor 205) that is adjacent to the skin surface 220 of the wearer. In some cases, the wristband is located immediately after the wrist bone on a posterior side of the wrist. In such cases, the recessed portion 215 may be located on the inside of the wrist and immediately after the wrist or at least a distance away from the wrist.

The recessed portion 215 may funnel vapor 225 into the biosensor 205 based on the design of the recessed portion 215. For example, the recessed portion 215 may include an elevated portion surrounding the recessed portion 215 where the elevated portion is a perimeter (e.g., outer boundary) of the recessed portion 215. The recessed portion 215 may be an example of a portion of the material of the housing material 210 that is removed. Thus the recessed portion 215 may be configured to funnel in a quantity of reactants (e.g., vapor 225) greater than a quantity of reactants able to be funneled into the biosensor 205 without the recessed portion 215.

The recessed portion 215 may be configured to capture the vapor 225 evaporating from the skin surface 220 of the wearer. In some cases, the recessed portion 215 is located a distance away from the skin surface 220 of the wearer. For example, the recessed portion 215 may not be in contact with the skin surface 220 of the wearer. In such cases, the recessed portion 215 captures the vapor state (e.g., vapor 225) of the transdermal reactant evaporating from the skin surface 220.

In other examples, the recessed portion 215 may be in direct contact with the skin surface 220 of the wearer. In such cases, the recessed portion 215 may capture a liquid state of the vapor 225 or condensed vapor 225. The biosensor 205 may be able to detect vapor 225 or the sweat.

The vapor 225 may be an example of alcohol. Based on physiological processes of the body, the wearer may get rid of (e.g., excrete) the alcohol via evaporation from the skin surface 220. The vapor 225 (e.g., alcohol) may evaporate from the skin surface 220, be captured in the recessed portion 215 of the biosensor 205, and may react with the biological enzymes and other components within the housing material 210. In such cases, the chemical reaction within the biosensor 205 occurs where the vapor 225 reacts with the biological enzyme. The chemical reaction may be an example of a biological reaction.

In conventional methods, a device including electronic circuitry may detect metabolites. For example, alcohol sensors (e.g., a breathalyzer) may necessitate liquid sensing, thereby inducing false positive because sweat, saliva, and components other than ethanol interfere with the conductivity. Liquid sensing may also introduce variation because of scientifically recognized individual variance in overall liquid (e.g., sweat) composition. However, the biosensor 205 may detect raw ethanol vapor 225 without the interference of other chemical compounds (e.g., salts or volatile compounds) that may induce false positives. In some examples, oxygen may be captured by the recessed portion 215 in which the oxygen may enhance reactivity with the biological enzymes within the biosensor 205. In other cases, oxygen may be unreactive with the biological enzymes within the biosensor 205, making the enzyme within the biosensor 205 to be more selective than conventional methods. In some cases, 1-5% of alcohol consumed may evaporate off the skin surface 220 unchanged.

Figure 3:
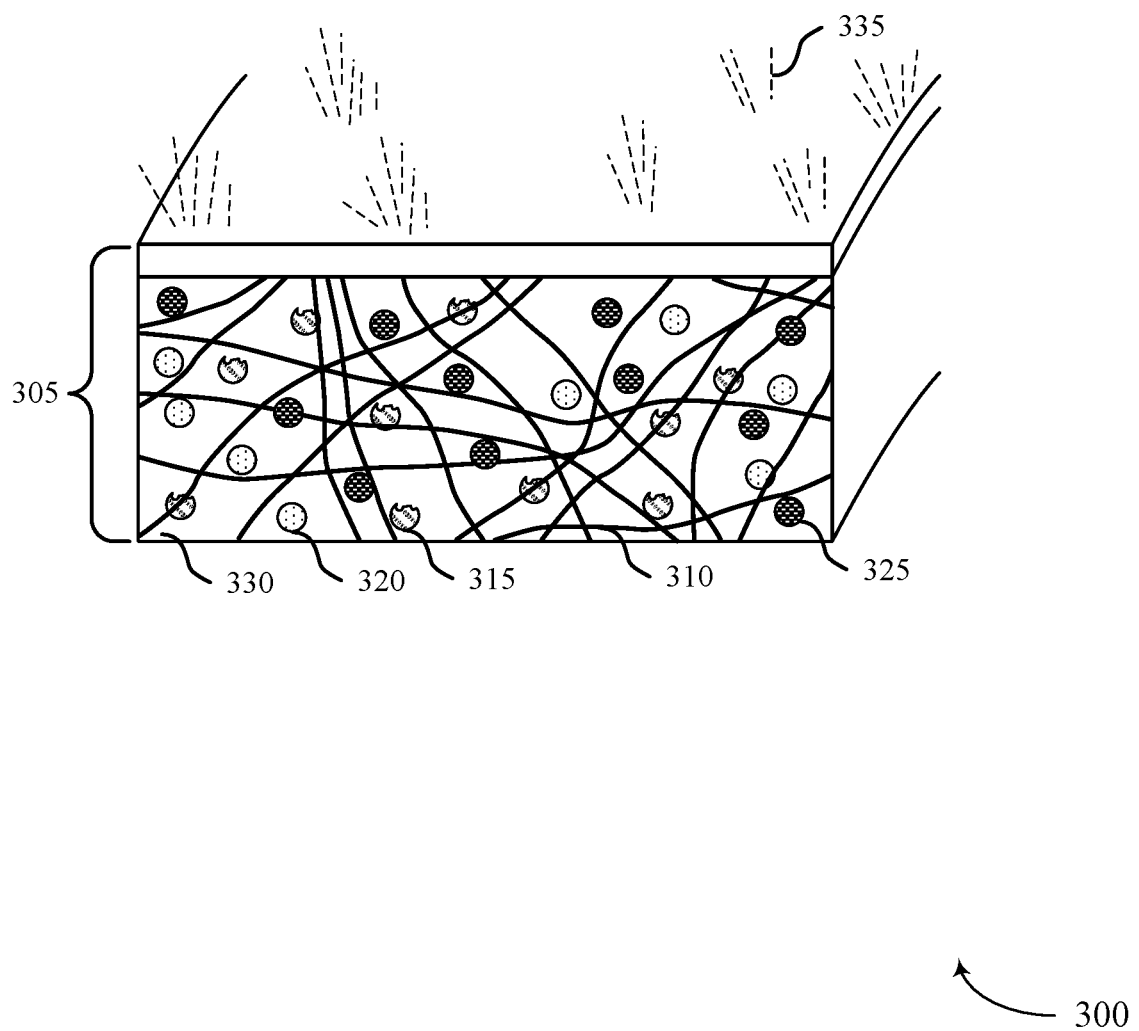
FIG. 3 illustrates a biosensor in accordance with aspects in the present disclosure.

FIG. 3 illustrates a biosensor 300 in accordance with aspects in the present disclosure. The biosensor 300 includes a housing material 305, a nanocellulose material 310, an enzyme 315, a luminescent material 320, and a fluorophore 325. The biosensor 300 and the housing material 305 may each be an example of the biosensor and housing material described with reference to FIGS. 1 and 2. The biosensor 300 may also include a solvent 330. In accordance with various examples, biosensor 300 may be used to detect transdermal reactants.

The nanocellulose material 310 may be disposed within the housing material 305. The housing material 305 may include a clear, polymeric material of the wristband other than the nanocellulose material 310. In some cases, the nanocellulose material 310 is bacterial nanocellulose. Bacterial cellulose may be a pure form of cellulose that is a nanomaterial. In some cases, bacterial cellulose is produced by a species of bacteria such as *Acetobacter, Gluconacetobacter*, and *Agrobacterium*. In such cases, the nanocellulose material 310 may be a biomaterial. For example, the nanocellulose material 310 may be grown with a strain (e.g., species) of bacteria, the cellulose may be harvested, and the cellulose may be applied in the form of nanocellulose material 310. In some cases, the nanocellulose material 310 may form micelles and serve as a surfactant.

The nanocellulose material 310 may produce light scattering effects. For example, the nanocellulose material 310 may serve as an amplifier for photons. As the chemical reaction occurs between the enzymes and compounds entrapped within the nanocellulose material 310, the nanocellulose material 310 may amplify the chemical change, color change, or electrical change to visibly change the appearance of the biosensor 300. The chemical reaction may be an example of a biological reaction. In some case, the nanocellulose material 310 may diffuse (e.g., allow to pass through unused) compounds (e.g., oxygen) which are not required for the chemical reaction through the nanocellulose material 310 and entrap the compounds (e.g., enzymes 315) required for the chemical reaction. For example, oxygen may be required for the catalysis of ethanol to formaldehyde and hydrogen peroxide by alcohol oxidase. The nanocellulose material 310 may distribute chemical compounds over an area of the biosensor 300 while still transmitting the chemical compounds. Chemical compounds may be an example of biological compounds.

The fibrils of the nanocellulose material 310 (e.g., bacterial cellulose) may be thinner than human hair and woven by the bacteria to create a web that may entrap enzymes 315 and liquid while still allowing the entry of small molecules (e.g., oxygen) from the surrounding environment. For example, the nanocellulose material 310 may entrap enzymes 315, provide noncovalent bonding between the enzyme 315 and the substrate (e.g., housing material 305), and increase the stability of the biosensor 300 to allow for two or more compounds to react. The reaction may be induced by the proximity of the compounds to each other based on the matrix network of the nanocellulose material 310.

In some cases, the nanocellulose material 310 may be compatible with the solvent 330 and the enzyme 315. The nanocellulose material 310 may be embedded within the solvent 330. For example, the solvent 330 may be multiple solvents in solution, mixture, or micelle formations. The solvent 330 may include low molecular weight organic solvents such as ethyl acetate or acetone as well as high molecular weight inorganic solvents such as phthalates. In some cases, the solvent 330 may be nonreactive with the enzyme 315. In some cases, a portion of solvent 330 may be miscible with water and the enzyme while other portions of solvent 330 are immiscible with water and the enzyme.

The enzyme 315 may be entrapped within the nanocellulose material 310. Enzyme immobilization may be due to the small size of pores and tortuous nature of the matrix (e.g., nanocellulose material 310) and surrounding compounds. Enzyme 315 immobilization may also be due to the ability to keep the enzyme 315 situated, stable, and ready for activation within the nanocellulose material 310. Thus the enzyme 315 may be entrapped in the nanocellulose material 310 to prevent the enzyme 315 from falling through the housing material 305.

The enzyme 315 may produce a chemical product when exposed to a vapor or liquid (e.g., ethanol). A chemical product may be an example of a biological product. In some cases, the enzyme 315 is alcohol oxidase. Alcohol oxidase may be an example of an octameric protein. In some cases, alcohol oxidase does not require a cofactor for the reaction with ethanol. When alcohol oxidase metabolizes (e.g., reacts with) ethanol, hydrogen peroxide is produced. Thus, hydrogen peroxide is the chemical product that the enzyme 315 produces when the enzyme 315 is exposed to ethanol.

The nanocellulose material 310 may hold the enzyme 315 near the ethanol, thereby allowing the reaction to happen at a faster rate. The alcohol oxidase may be surrounded with water and a buffer solution. In such cases, hydrogen peroxide may move between the alcohol oxidase and water. The solvent 330 may also move between the alcohol oxidase and water.

In some cases, hydrogen peroxide may start a reaction chain such that hydrogen peroxide serves as a catalyst to produce visible light 335 (e.g., a glow effect) from the chemical reaction. For example, the luminescent material 320 and fluorophore 325 within the nanocellulose material 310 may emit visible light 335 upon a chemical reaction with the hydrogen peroxide. In some cases, the nanocellulose material 310 may hold the molecules (e.g., luminescent material 320, fluorophore 325, or both) necessary to react with hydrogen peroxide near hydrogen peroxide, thereby allowing the reaction to happen at a faster rate.

In some examples, the luminescent material 320 is a chemiluminescent or bioluminescent material. In some cases, the luminescent material 320 is CPPO, bis(2,4,6-trichlorophenyl)oxalate (TCPO), or bis(2,4-nitrophenyl)oxalate (DNPO). The luminescent material 320 may be an example of an oxalate diester. The chemical reaction between CPPO and hydrogen peroxide may not require ultraviolet (UV) light and may result in a color change (e.g., visible light 335 via a glow). Thus the product of the chemical reaction may be seen by the naked eye. The CPPO may serve as an oxalate in which high energy molecules combine with hydrogen peroxide and produce an intermediate. The intermediate may react with the fluorophore 325. The luminescent material 320 and fluorophore 325 may each be an example of a chemical or biological reactant that produces luminescence in the presence of a ligand.

Fluorophores 325 may be a fluorescent chemical compound that can re-emit light in the visible spectrum when energized. For example, the fluorophore 325 may serve as a dye that pulls electrons from the intermediate and converts the electrons into photons. In some cases, the fluorophores 325 may be independent of the chemical reaction between CPPO and hydrogen peroxide. The color emitted based on the chemical reaction may be tuned by the addition of fluorophores 325. For example, the addition of multiple fluorophores 325 may emit a white glow.

The chemical reaction between the CPPO and hydrogen peroxide may be dependent on the solvent 330. The solvent 330 may be an organic solvent or an inorganic solvent that facilitates the chemical reaction of the luminescent material 320 and the chemical product (e.g., hydrogen peroxide). For example, the solvent 330 may be an example of a multi-solvent system that comprises phthalate or ethyl acetate. A solvent 330 that is an organic solvent may be miscible with the phthalate system and may be used for doping. In some cases, a double solvent system may occur which results from surfactant activity of the nanocellulose material 310. For example, a first solvent may be phthalate, and a second solvent may be a low molecular weight organic solvent and water. The phthalate may be an inorganic solvent that is immiscible with water. In some case, the enzyme 315 may require water.

In such cases, the output from first system (e.g., hydrogen peroxide produced from ethanol reacting with alcohol oxidase) may be miscible with the second system (e.g., phthalate buffer and CPPO). For example, the proximity of hydrogen peroxide to other compounds (e.g., CPPO) may increase the mobility of the hydrogen peroxide and rate of the reaction. In such cases, hydrogen peroxide may move from the aqueous solution that produced hydrogen peroxide into the non-aqueous solution to enable the reaction between hydrogen peroxide and CPPO, thereby producing visible light.

In some cases, an oxidase (e.g., CPPO) may be associated with chromogenic molecules via intermolecular forces. The intermolecular forces may include Van der Waals forces, crowding, formation of micelles, or a combination thereof. The intermolecular forces may also include cellulosome hierarchical assembly. In some oxalate based chemiluminescence system, the emission of light is produced via chemical reactions with an oxalate (e.g., luminescent material 320). The reaction may be accelerated by the addition of a base catalyst (e.g., sodium acetate, a salicylate, or both). The signal may be amplified via the nanocellulose material 310 (e.g., nanocellulose micelle formation and photon scattering). In some cases, polymer composites contribute to scintillating (e.g., sparkling or shining) optics.

Figure 4:
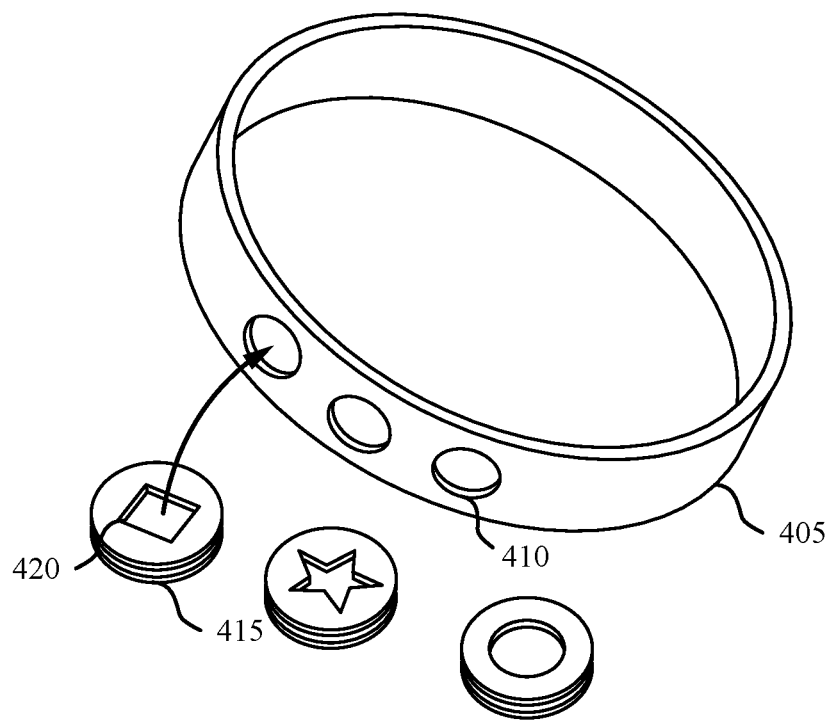
FIG. 4 illustrates a modular biosensor system in accordance with aspects in the present disclosure.

FIG. 4 illustrates a modular biosensor system 400 in accordance with aspects in the present disclosure. The modular biosensor system 400 includes a housing material 405, module inserts 410, biosensor modules 415, a shape 420. The housing material 405 may be an example of the housing material described with reference to FIGS. 1-3. In accordance with various examples, modular biosensor system 400 may be used to detect transdermal reactants.

The housing material 405 may include one or more module inserts 410. The housing material 405 may be an example of a wristband, a necklace, a handheld sensor, or a combination thereof. The module inserts 410 may be configured to house a biosensor module 415. For example, the biosensor modules 415 may be removably coupled with the module inserts 410, thereby allowing the biosensor modules 415 to be inserted into the module inserts 410 or removed from the module inserts 410. In such cases, the modular design of the modular biosensor system 400 may be dispensable for other biosensor wearable devices. The biosensor modules 415 may be an example of a tile to house biosensors (e.g., biosensor modules 415) such as a pendant that may be implemented into the module insert 410 of the housing material 405 (e.g., a wristband, a necklace, etc.).

In some cases, the biosensor module 415 may be modularized in order to remove the biosensor module 415 from the housing material 405 and insert other biosensor modules 415 that may detect other biomarkers. Thus the biosensor module 415 may increase the different types of biometric data that may be monitored accurately, securely, and non-invasively. In such cases, the user may customize the modular biosensor system 400 in a manner unique to the needs or interests of the user. The user may decide which information to monitor and how to visualize the results. The user may slide biosensor modules 415 into the module inserts 410 according to the need of the user. In some cases, each biosensor module 415 may include a shape 420 corresponding to the which information to monitor or how to visualize the results.

For example, the biosensor module 415 may be able to detect BAC, glucose, microbiota, drug levels, disease, or a combination thereof. The biosensor module 415 may also be able to detect aerosol toxins, infection, plant toxins, spoiled food, UV radiation, or a combination thereof. In such cases, the detectable reactant comprises ethanol, glucose, dermal microbiota, toxins, a chemical or biological compound associated with a medical condition, nutrients, metabolic by-products, hormones, environmental ligands, or a combination thereof.

The biosensor modules 415 may each comprise a matrix material, an enzyme within the matrix material that produces a chemical or biological product when exposed to a detectable reactant, and an indicator material that indicates a change upon a reaction with the chemical or biological product. The matrix material may be an example of the nanocellulose material as described with reference to FIG. 3. The enzyme may be an example of the enzyme as described with reference to FIG. 3.

The biomolecules (e.g., enzymes) may be immobilized within the matrix material. The matrix material may be semi-permeable or impermeable materials to direct analytes (e.g., detectable reactant) to the biosensor module 415. The matrix material may include bacterial cellulose, chitosan, glutaraldehyde, agarose, alginate, kombucha pellicle, or a combination thereof. For example, chitosan and glutaraldehyde may immobile the enzyme via covalent bonding via chemical associations. Chitosan may be made into a film or a tunable gel. Glutaraldehyde may bridge amino groups between biomolecules by using a reagent for crosslinking proteins.

In some examples, bacterial cellulose, agarose, and alginate may immobilize the enzyme via pore size and molecular entanglement. Bacterial cellulose may be made into a film, a gel, or combined with filter paper. In some cases, bacterial cellulose may include tunable bonding properties such as cellulose specific enzymes, chemical modification, and nanoparticle decoration. Agarose may immobilize the enzyme via gel entrapment by microwave induced polymerization. Alginate may immobilize the enzyme via salt induced cross-linkage of polymers to allow for non-covalent entrapment of enzymes. The matrix material may further include materials such as microfibrillar cellulose, gellan gum, gelatin, collagen, agar, carrageenan, pectin, lecithin, or a combination thereof.

The indicator material may be an example of the luminescent material and fluorophore as described with reference to FIG. 3. The indicator material may visibly change by changing color, electrical properties, chemical properties, or a combination thereof. For example, the biosensor module 415 may change from invisible to visible. In other examples, biosensor module 415 may glow, change colors, or both.

In some examples, the biosensor module 415 may be integrated within electronic wearable devices (e.g., fitness trackers, smartwatches, and electronic tattoo). In such cases, connecting biosensors with electronic storage may enable long-term monitoring of biosensor data. The biosensor module 415 may include a tunable distance from the skin surface of the wearer for liquid capture, vapor capture, or both.

Figure 5:
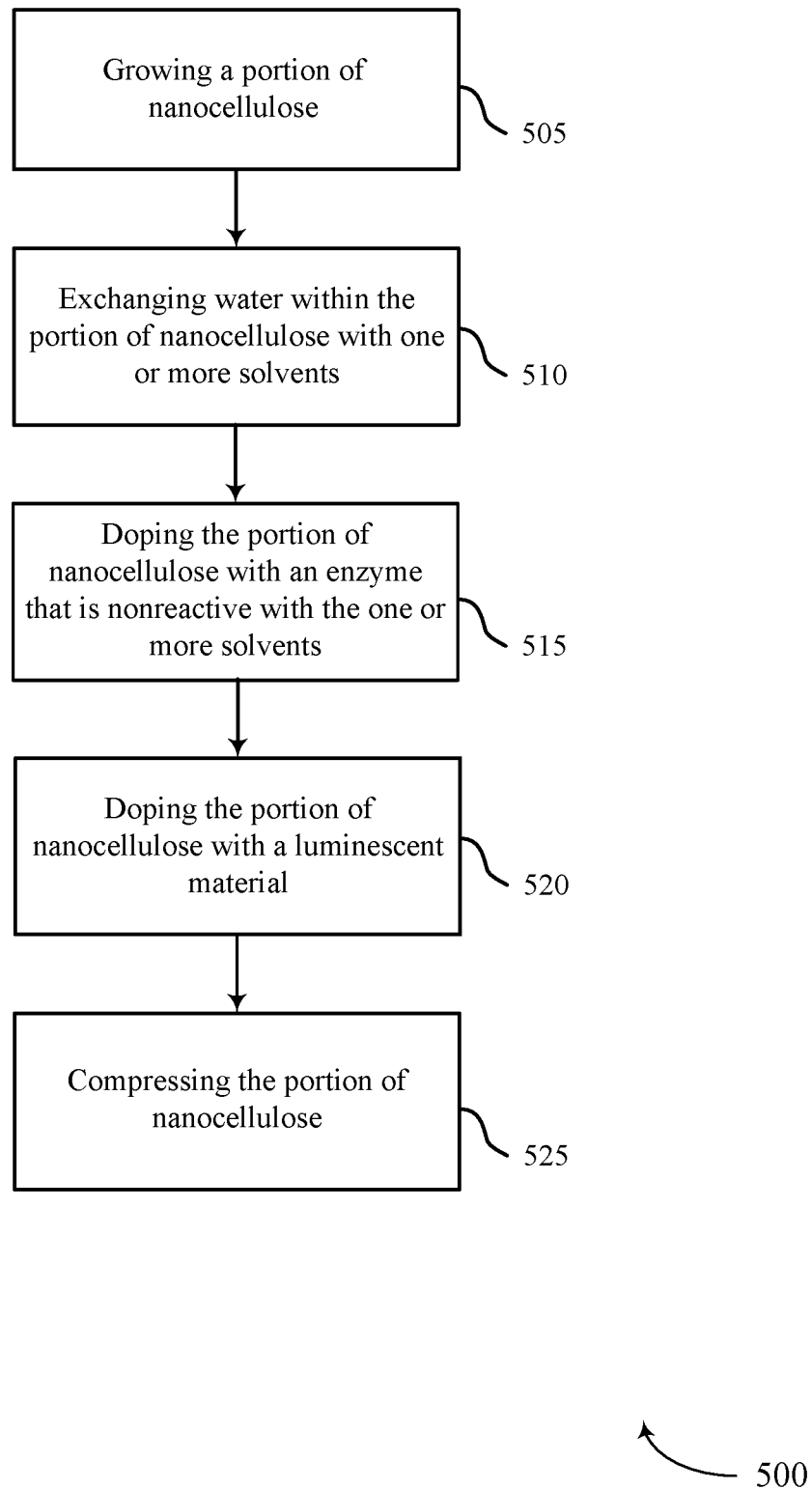
FIG. 5 illustrates a flowchart of methods for fabricating a biosensor in accordance with aspects in the present disclosure.

FIG. 5 illustrates a flowchart of methods for fabricating a biosensor in accordance with aspects in the present disclosure. The steps of method 500 may be an example of aspects of a method of formation of the particular biosensor described with reference to FIGS. 1-4.

At 505, the method may include growing a portion of nanocellulose. In some cases, the nanocellulose may be bacterial nanocellulose. Bacterial nanocellulose is 99% void space. Thus bacterial nanocellulose is predominately made of water. After the bacterial nanocellulose is grown, the bacterial nanocellulose may be treated to remove non-cellulose pieces and restabilize the pH of the bacterial nanocellulose. For example, the bacterial nanocellulose may be washed with sodium hydroxide or potassium hydroxide and then placed in deionized water for more than 48 hours. The wet cellulose may be cut into squares. The thickness of the squares may include a minimum thickness of 1.5 cm.

At 510, the method may include exchanging water within the portion of nanocellulose with one or more solvents. In some cases, the one or more solvents comprise a phthalate or acetone. In other examples, the one or more solvents may be tert-butyl alcohol or ethyl acetate. At 510, the method may be an example of a solvent exchange. During the solvent exchange, water may be exchanged with a lower molecular weight solvent.

The bacterial nanocellulose may collapse when water is removed via drying or evaporation, therefore a lower molecular weight solvent may be needed to preserve the fibril network. The bacterial nanocellulose may include a high mechanical and structural strength due to the complex network of the nanofibers. In such cases, the lower molecular weight solvent may be needed to maintain the orientation of nanofibers as the bacterial nanocellulose dries (e.g., loses water) instead of the material of the bacterial nanocellulose flattening to an assemblage of fibers that are aligned in one or two directions.

In order to remove the water, a solvent may be chosen that is compatible (e.g., unreactive, miscible) with the buffered o-oxalate system (e.g., hydrogen peroxide reacting with CPPO). The solvent may also be unreactive with the enzyme. For example, the solvent (e.g., phthalate or ethyl acetate) may be unreactive with alcohol oxidase. The solvent exchange may be performed for six days or more from deionized water to a low molecular weight solvent that is miscible with the phthalate/CPPO system and non-reactive with alcohol oxidase. For example, the solvent of ethyl acetate may be miscible with the phthalate/CPPO system and may be miscible with water. The removal of water from the hydrophilic nanocellulose may allow for doping with immiscible solvents and luminescent materials. The solvent exchanged nanocellulose may afford a double solvent system that allows for a water and enzyme solution to be in close proximity to immiscible solvents and luminescent materials.

At 515, the method may include doping the portion of nanocellulose with an enzyme that is nonreactive with the one or more solvents. For example, nanocellulose may be doped with a phthalate based solvent, and then the enzyme may be added to the system. The enzyme may be entrapped within the bacterial nanocellulose based on doping the nanocellulose with the enzyme.

At 520, the method may include doping the portion of nanocellulose with a luminescent material. The luminescent material may comprise an oxalate and a fluorophore. In some cases, doping the portion of nanocellulose with a luminescent material may occur over varying time frames. In some examples, doping the portion of nanocellulose with a luminescent material may include doping cubes of solvent exchanged bacterial nanocellulose with a solution of phthalate, CPPO, and fluorophore. In some cases, salicylic acid and bases are added to enhance an intensity of the reaction.

At 525, the method may include compressing the portion of nanocellulose. The portion of nanocellulose may be compressed with active compounds. In some cases, the portion of nanocellulose may be compressed after the addition of the enzyme (e.g., alcohol oxidase), thereby increasing the ability to entrap the enzyme and increasing the refractive properties of the nanocellulose material. Compressing the portion of nanocellulose may result in a tougher membrane to withstand drying conditions and limit irregular collapse of the nanocellulose. A mold may be used to press the doped nanocellulose into form (e.g., shape).

In some examples, the method may further include stamping a shape from the compressed portion of nanocellulose. The shapes may be three-dimensional (3D) printed to enable tailored sensing of vapor or liquid compounds at varying temperatures and volumes. For example, each biosensor may include a shape that is stamped into the compressed portion of nanocellulose. The shape may correspond to the monitored information or the means to visualize the results.

At 525, the method may further include patterning a shape onto the compressed portion of nanocellulose. The pattern may allow for portions of the nanocellulose to be tightly compressed and transparent, localizing and condensing the solution of phthalate, CPPO, and fluorophore into raised areas surrounding each compressed area, thereby increasing the physical separation of the enzymatic reaction.

The compression of the nanocellulose may contribute to scintillating (e.g., sparkling or shining) optics. The nominal thickness of the compressed area may be less than 0.5 mm, and the nominal thickness of the raised areas may be greater than 3 mm. Compressing the portion of nanocellulose may result in greater barrier properties of the nanocellulose, thereby increasing the physical separation of the enzymatic reaction with alcohol from the transduction of hydrogen peroxide through CPPO or other oxalates.

Concentrated alcohol oxidase in buffered solution may be added to the compressed areas. In some examples, concentrated alcohol oxidase in buffered solution may be added to the raised areas. Following the addition of concentrated alcohol oxidase in buffered solution, a dispersed, solvent exchanged bacterial nanocellulose may be added to the compressed area, the raised area, or both. The dispersed, solvent exchanged bacterial nanocellulose may be prepared by grinding or sonication at a temperature below 0° C. The compressed areas may prevent enzyme loss through the nanocellulose material, and the addition of the dispersed, solvent exchanged bacterial nanocellulose may entrap the enzyme (e.g., alcohol oxidase).

In some examples, the method of fabricating the biosensor may further include doping a portion of the stamped nanocellulose with an enzyme that is nonreactive with the one or more solvents. For example, the method may include adding dispersed and solvent exchanged nanocellulose onto the enzyme and biosensor. In some implementations the one or more solvents comprise a phthalate or ethyl acetate.

EXAMPLES

In order to illustrate the disclosure, the following examples are included. However, it is to be understood that these examples do not limit the disclosure and are only meant to suggest exemplary methods of practicing the disclosure.

In some examples, the disclosed biosensor may be housed in macrocellulose and positioned a fixed distance from a standing source of alcohol evaporating onto the sensor, indicating the vapor quantity through marked changes (e.g., brightness) in visible luminescence for 90 minutes or more.

In some examples, enzyme may be added at quantities at least two-fold greater than the required number of active units to instantly catalyze the amount of ethanol in both liquid and vapor phases.

In some examples, the biosensor may include enzyme(s) with an optimal reactivity temperature at 98.6° F. (i.e., human body temperature). The disclosed biosensor may be housed in a location proximal to human skin to afford an increased rate of reaction with the enzyme and substrate.

In some examples, concentrated sodium acetate buffer may be added to concentrated enzyme stock prior to doping to the biosensor.

In some examples, concentrated salicylic acid stock may be added to concentrated enzyme stock prior to doping the biosensor.

In some examples, the disclosed biosensor may be applied directly to the underside of the wrist directly to the skin with a polymeric housing and indicated alcohol presence through luminescence.

In some examples, the disclosed biosensor may be elevated above the wearer's skin at a tuned distance by a housing made of a waterproof material. It may be understood that this housing contained an external bevel surrounding the biosensor and may assist in preventing false positives due to an external environmental ligand.

In some examples, the disclosed biosensor may be applied to the back of the wearer's hand or upper arm and produced less luminescence than identical biosensors applied to the wrist area. It may be understood that the scientific literature asserts the wrist as an anatomical location where 1-5% of pure ethanol per 1 $cm^2$ area of skin surface of the wearer is excreted transdermally from total alcohol consumed by the wearer.

In some examples, a slurry of nanocellulose may be applied after addition of the alcohol oxidase. In such cases, the general spacing between nanofibrils may be random and smaller than the octameric protein used, thereby enabling entrapment.

In some examples, the disclosed biosensor may be fabricated and stored at room temperature for up to 10 days and activated after exposure to the ligand, matching scientific literature assertion of the enzyme half-life for optimal reactivity at room temperature. In such cases, reactivity (i.e., brightness) may decrease after a period of 10 days.

In some examples, the disclosed biosensor may be designed as a bracelet form factor where the results of the luminescence are visible privately to the wearer.

In some examples, the housing material and the sensor material are biodegradable and able to completely degrade in open exposure to the environment within 30 days.

In some examples, 1 $cm^3$ of bacterial cellulose may be step-wise solvent exchanged to ethyl acetate before being doped with excess luminescent material and compressed with a diamond-studded pattern. In some examples, a concentrated, buffered enzyme may be added to the well-like compressions of the stamp. The 1 $cm^3$ of bacterial cellulose may be solvent exchanged from water to acetone using an excess amount of acetone over 48 hours. The 1 $cm^3$ of bacterial cellulose may be solvent exchanged from acetone to ethyl acetate over 72 hours. The excess luminescent material used to dope the 1 $cm^3$ of bacterial cellulose may be a dibutyl phthalate/CPPO/fluorophore system in a range from 1-24 hours.

In some examples, the disclosed biosensor may be pressed with a repeating pattern, thereby resulting in optical scintillation effects.

In some examples, the disclosed biosensor may be compressed over 95% of its original volume, thereby increasing its barrier properties for ethanol.

In some examples, the recession within the housing of the disclosed biosensor may comprise a larger surface area than the biosensor and may be able to capture a higher physical quantity of ethanol vapor, thereby resulting in brighter luminescence as compared with a flat housing.

In some examples, the individual nanocellulose modules may be insertable into custom modular inserts.

In some examples, multiple enzymes may be used and activated within a single nanocellulose matrix material.

In some examples, multiple representations of colors on the visible spectrum may be activated by the disclosed biosensor.

In some examples, multiple enzymes and multiple colors may be utilized and activated within a single nanocellulose matrix material.

In some examples, the housing of the disclosed biosensor housed multiple biosensors comprised of multiple enzymes and luminescent materials.

In some examples, the fluorophores in the luminescent material may be combined to luminesce as different colors including red, white, blue, orange, green, and purple.

In some examples, the disclosed biosensor may be applied to a user's skin in an inactivated state where the disclosed biosensor became active upon removal of a preservative cover.

In some examples, the biosensor may be in a recessed housing, with an impermeable polymeric covering, preventing ethanol vapor contact with biosensor until the user removed the impermeable polymeric covering to allow for activation of the disclosed biosensor.

In some examples, the disclosed biosensor may be selectively tuned through choice of the enzyme (e.g., alcohol oxidase) and tested with a less reactive but scientifically known reactive ligand (e.g., propanol) that may trigger the reaction (e.g., luminescence) but at a reduced level of reactivity (e.g., brightness).

In some examples, a nanocellulose slurry may be solvent exchanged and combined with luminescent materials and enzyme to create a liquid state sensor and then applied to a ligand-excreting surface in liquid form (e.g., ink, tattoo).

In some examples, the luminescent materials and enzyme may be doped onto a cube of nanocellulose which was compressed to decrease molecular spacing between reactants and enhance reactivity.

In some examples, the nanocellulose may be conditioned (e.g., with electrical currents, varying concentrations of oxygen, material adjuncts) to selectively tune the nanocellulose matrix to enhance reaction efficiency and optical properties of resulting reaction.

In some examples, the disclosed biosensor may be applied step-wise to an existing wearable product, and reactivity may be demonstrated.

In some examples, the disclosed biosensor may be fabricated and assembled in temperatures not exceeding 4° C.

In some examples, the disclosed biosensor may be fabricated and assembled at room temperature.

The disclosed biosensor may be used to study amounts of ethanol vapor evaporated from a 1 $cm^2$ area of a skin surface of the wearer. The disclosed biosensor may be able to detect nanogram levels of ethanol vapor. The biosensor may be able to visibly luminesce the presence of microgram quantities.

It may be understood that 1-5% of ethanol consumed may be emitted from the skin unchanged. It may be understood that the kinetics of transdermal alcohol exchange may be anatomically specific and linked to volume of blood present in relation to thickness of skin. It may be understood that a generalized flow rate of total vapor leaving the skin may be 180 ul/hr. It may be understood that the proximity of the biosensor impacts effective capture and transduction of this transdermal vapor.

It may be understood that the rate of ethanol vapor emission from 1 $cm^2$ of human skin may be approximated to a range of 1.44 ug/hr-7.20 ug/hr corresponding to 1-5% transdermal emission rates at a steady state of 0.08 g/dL blood alcohol concentration at vapor flow rate of 180 ul/hr.

In some examples, units of alcohol oxidase and molar concentrations of chemiluminescent material may be tuned according to a target range of molar concentrations of ethanol. It may be understood that decreasing or increasing units of alcohol oxidase or chemiluminescent material or both may afford sensors with varying responses to varying ethanol concentrations.

In some examples, ethanol availability may be calculated based on an assumption that a person may be given 88.7 ml (e.g., 3 fl oz) of 80 proof (e.g., 40%) alcohol which may equal approximately 28,000 mg total ethanol consumed. One percent of the 28,000 mg of ethanol consumed may be equal to a minimum of 280 mg of ethanol excreted through the skin. There may be approximately 19,0000 $cm^2$ of a total surface area of the skin surface. Thus, if 1% of the total ethanol is excreted, an average of 0.0147 mg (e.g. 14.7 ug) of total ethanol may be excreted for any 1 $cm^2$ area of the skin surface.

Prior publications may show that these levels can be closely correlated mathematically based on repeated sampling in the same physical location. Table 1 may represent the temporal relationship between BAC levels and TAC equivalent levels.

TABLE 1

| Blood Alcohol Concentration (BAC) | Transdermal Alcohol Concentration (TAC) Equivalent |
|---|---|
| 0.3 | 0.1 |
| 0.4 | 0.3 |
| 0.6 | 0.4 |
| 0.7 | 0.7 |
| 0.9 | 0.8 |

The above specification, examples, and data provide a complete description of the structure, features, and use of exemplary implementations of the invention. Since many implementations of the invention may be made without departing from the spirit and scope of the invention, the invention resides in the claims hereinafter appended. Furthermore, structural features of the different implementations may be combined in yet another implementation without departing from the recited claims.

The invention claimed is:

1. A biosensor, comprising:
   a housing material;
   a nanocellulose material disposed within the housing material;
   an enzyme entrapped within the nanocellulose material that produces a chemical or biological product when exposed to a substance in a vapor or liquid; and
   a luminescent material within the nanocellulose material that emits visible light upon a chemical or biological reaction with the chemical or biological product.

2. The biosensor of claim 1, wherein the vapor or liquid comprises ethanol.

3. The biosensor of claim 1, wherein the enzyme comprises alcohol oxidase.

4. The biosensor of claim 1, wherein the nanocellulose material comprises bacterial nanocellulose.

5. The biosensor of claim 4, wherein the bacterial nanocellulose immobilizes the enzyme within the bacterial nanocellulose.

6. The biosensor of claim 1, wherein the chemical or biological product comprises hydrogen peroxide.

7. The biosensor of claim 1, wherein the luminescent material comprises an oxalate and a fluorophore, wherein the luminescent material is a chemiluminescent or bioluminescent material.

8. The biosensor of claim 1, further comprising one or more solvents that facilitate the chemical or biological reaction of the luminescent material and the chemical or biological product.

9. The biosensor of claim 1, wherein the housing material comprises a polymer.

10. The biosensor of claim 1, wherein the housing material forms a wristband.

11. The biosensor of claim 10, further comprising a recessed portion disposed on a side of the wristband that is adjacent to a skin surface of a wearer, wherein the recessed portion is configured to capture the vapor or liquid evaporating from the skin surface of the wearer.

12. The biosensor of claim 1, wherein the biosensor is biodegradable, wherein the biosensor is a transdermal biosensor.

13. A method for fabricating a biosensor, comprising:
   growing a portion of nanocellulose;
   exchanging water within the portion of nanocellulose with one or more solvents;
   doping the portion of nanocellulose with an enzyme that is nonreactive with the one or more solvents;
   doping the portion of nanocellulose with a luminescent material; and
   compressing the portion of nanocellulose.

14. The method of claim 13, further comprising stamping a shape from the compressed portion of nanocellulose or patterning a shape onto the compressed portion of nanocellulose.

15. The method of claim 13, wherein:
   the one or more solvents comprise a phthalate or ethyl acetate; and
   the luminescent material comprises an oxalate and a fluorophore.

16. A modular biosensor system, comprising:
   a housing material comprising one or more module inserts; and
   one or more biosensor modules removably coupled with the one or more module inserts, wherein the one or more biosensor modules each comprise:
   a nanocellulose material;
   an enzyme within the nanocellulose material that produces a chemical or biological product when exposed to a detectable reactant; and
   an indicator material that indicates a change upon a reaction with the chemical or biological product.

17. The modular biosensor system of claim 16, wherein the nanocellulose material immobilizes the enzyme within the matrix material.

18. The modular biosensor system of claim 16, wherein the detectable reactant comprises ethanol, glucose, dermal microbiota, toxins, a chemical or biological compound associated with a medical condition, nutrients, metabolic by-products, hormones, environmental ligands, or a combination thereof.

19. The modular biosensor system of claim 16, wherein the indicator material that indicates the change comprises a color change, an electrical change, a chemical change, or a combination thereof.

20. The modular biosensor system of claim 16, wherein the nanocellulose material further comprises bacterial cellulose, chitosan, glutaraldehyde, agarose, alginate, kombucha pellicle, or a combination thereof.

* * * * *